United States Patent [19]
Narita et al.

[11] Patent Number: 5,917,099
[45] Date of Patent: Jun. 29, 1999

[54] PREPARATION OF METHYL CHLORIDE

[75] Inventors: Tomomi Narita; Hiroyuki Kobayashi; Yukinori Satoh; Yoshihiro Shirota, all of Annaka, Japan

[73] Assignee: Shin-Etsu Chemical Co., Ltd., Japan

[21] Appl. No.: 09/078,714

[22] Filed: May 14, 1998

[30] Foreign Application Priority Data

May 14, 1997 [JP] Japan .................................. 9-139395

[51] Int. Cl.$^6$ .................................................. C07C 17/16
[52] U.S. Cl. ............................................................ 570/258
[58] Field of Search ............................................. 570/258

[56] References Cited

U.S. PATENT DOCUMENTS 4,922,043  5/1990  Petrosky .

OTHER PUBLICATIONS

Derwent Publications, Ltd., XP–002071593 Aug. 1995.

*Primary Examiner*—Alan Siegel
*Attorney, Agent, or Firm*—Millen, White, Zelano, & Branigan, P.C.

[57] ABSTRACT

Methyl chloride is prepared by effecting liquid-phase reaction between hydrogen chloride and methanol in the absence of a catalyst. The reaction is effected in divided stages including at least an early stage and a last stage. The early stage of reaction is effected in a stoichiometric excess of hydrogen chloride. The last stage of reaction is effected in a stoichiometric excess of methanol. The invention is industrially advantageous in that methyl chloride can be prepared at a high conversion of hydrogen chloride while suppressing the formation of dimethyl ether by-product.

9 Claims, 2 Drawing Sheets

PREPARATION OF METHYL CHLORIDE

This invention relates to a process for preparing methyl chloride by reacting hydrogen chloride with methanol.

BACKGROUND OF THE INVENTION

A number of processes have been proposed for the preparation of methyl chloride from reaction of hydrogen chloride with methanol. Reaction is generally carried out in a vapor or liquid phase in the presence or absence of a catalyst. Most known processes use catalysts for promoting reaction and carry out reaction in an atmosphere containing a stoichiometric excess of hydrogen chloride relative to methanol.

However, methyl chloride production processes including the above-mentioned ones, which are currently implemented in the industry, have several drawbacks. The process of effecting vapor-phase reaction in the presence of a catalyst is disadvantageous in that reaction temperatures as high as 300 to 450° C. cause more amounts of dimethyl ether and other decomposed products to be formed than other processes and requires the catalyst to be replaced or regenerated. This process requires gaseous hydrogen chloride which is anhydrous or dried to a nearly anhydrous extent and gaseous methanol as the reactants.

The process of effecting liquid-phase reaction in the presence of a catalyst is disadvantageous in that the reaction temperature is higher than in the liquid-phase non-catalyzed process, more dimethyl ether by-product is formed due to the use of the catalyst, and the catalyst must be periodically renewed because impurities accumulate in the catalyst.

While hydrogen chloride by-product obtained in a silicone manufacturing plant contains silicones and hydrogen chloride by-product resulting from other processes contains organic impurities, the use of such hydrogen chloride by-product as the reactant is not suitable for the catalyzed vapor- or liquid-phase processes because the catalyst can be deactivated by silicones or other organic impurities. A limit is imposed on the reactants which can be used in these processes.

The process of effecting liquid-phase reaction in the absence of a catalyst suffers from a low reaction rate. Since methanol is reacted with an excess over stoichiometry of hydrogen chloride, the concentration of hydrogen chloride in the reactor exceeds the azeotropic concentration so that a substantial fraction of hydrogen chloride may be distilled off the reactor along with the methyl chloride gas produced, leading to a noticeably reduced utilization of hydrogen chloride.

Illustratively, U.S. Pat. Nos. 3,981,938, 4,220,609 and 4,922,043 describe a process for forming methyl chloride by reacting methanol with a stoichiometric excess or equivalent amount of hydrogen chloride. This process has the above-mentioned disadvantage that the concentration of hydrogen chloride in the reactor approaches the azeotropic concentration so that a large fraction of hydrogen chloride may be evaporated from the reactor along with the methyl chloride gas produced, leading to a noticeably reduced utilization of hydrogen chloride. An aqueous solution of unreacted hydrogen chloride in water by-product can be separated from the crude product gas by cooling, but this solution is corrosive and very difficult to treat, requiring an additional expense for disposal.

U.S. Pat. No. 4,935,564 discloses a process for preparing an alkyl halide by passing a hydrogen halide and a stoichiometric excess (typically about 20 to 200 mol % excess) of an alcohol in the absence of a catalyst in a single pass through a plug-flow reactor. As the amount of alcohol is increased (in stoichiometric excess relative to hydrogen halide), the amount of dimethyl ether by-product increases. As the amount of alcohol is reduced, the conversion of hydrogen chloride declines. It is difficult to determine optimum reaction conditions. A single stage of plug-flow reactor is insufficient in order to suppress formation of by-products and to increase the conversion of hydrogen chloride.

U.S. Pat. No. 5,202,512 describes a process for preparing a $C_1$–$C_4$ halogenoalkane by reacting a $C_1$–$C_4$ alkanol with a hydrogen halide in the presence of a catalyst. On account of the catalyst used, this process has drawbacks including increased by-products, attachment of an extra equipment for adding the catalyst, difficulty to control the catalyst concentration, deactivation of the catalyst by impurities in the starting hydrogen chloride, and treatment of the deactivated catalyst.

SUMMARY OF THE INVENTION

An object of the invention is to provide a process for preparing methyl chloride by reacting hydrogen chloride with methanol whereby methyl chloride is obtained at a high conversion of hydrogen chloride while suppressing the formation of dimethyl ether by-product.

According to the invention, reaction of hydrogen chloride with methanol to form methyl chloride is carried out in a liquid phase in the absence of a catalyst and in a system having at least two stages of reactors including an early stage and a last stage. The early stage of reaction is effected in a stoichiometrically excessive hydrogen chloride atmosphere to increase the reaction rate and to suppress the formation of dimethyl ether by-product. The last stage of reaction is effected in a stoichiometrically excessive methanol atmosphere to reduce the concentration of hydrogen chloride below the azeotropic concentration and to increase the conversion of hydrogen chloride. Since the formation of dimethyl ether is suppressed and the evaporation of hydrogen chloride is restrained by reducing the concentration of hydrogen chloride in the last stage reactor below the azeotropic concentration, the utilization of hydrogen chloride is outstandingly improved over the prior art processes. Since no catalyst is used, even a reactant containing an impurity capable of deactivating the catalyst can be used. Thus methyl chloride can be prepared in an industrially advantageous manner.

Briefly stated, the invention provides a process for preparing methyl chloride by effecting liquid-phase reaction between hydrogen chloride and methanol in the absence of a catalyst. The liquid-phase reaction is effected in divided stages including at least an early stage and a last stage. The early stage of liquid-phase reaction is effected in a stoichiometrically excessive hydrogen chloride atmosphere. The last stage of liquid-phase reaction is effected in a stoichiometrically excessive methanol atmosphere.

As compared with the prior art processes, the process of the invention has the following advantages.

(1) Since the reaction is effected in two or more divided stages, both the reaction rate and the conversion of hydrogen chloride can be improved. The amount of methanol which is excessive over stoichiometry can be reduced compared to that required in the single stage process. The amount of dimethyl ether by-product formed can be reduced. More particularly, in reaction prior to the last stage, the reaction rate is increased and formation of dimethyl ether is suppressed. In the last stage of reaction, water by-product can be selectively distilled out of the system while suppressing the evaporation of hydrogen chloride from the reactor. Thus the conversion of hydrogen chloride is significantly improved.

(2) Since no catalyst is used, extra equipment for adding the catalyst and the control of the catalyst concentration are unnecessary.

(3) A hydrogen chloride product containing silicones obtained from a silicone manufacturing plant and another hydrogen chloride product containing an impurity capable of deactivating the catalyst can be used as the reactant.

DETAILED DESCRIPTION OF THE INVENTION

Figure 1:
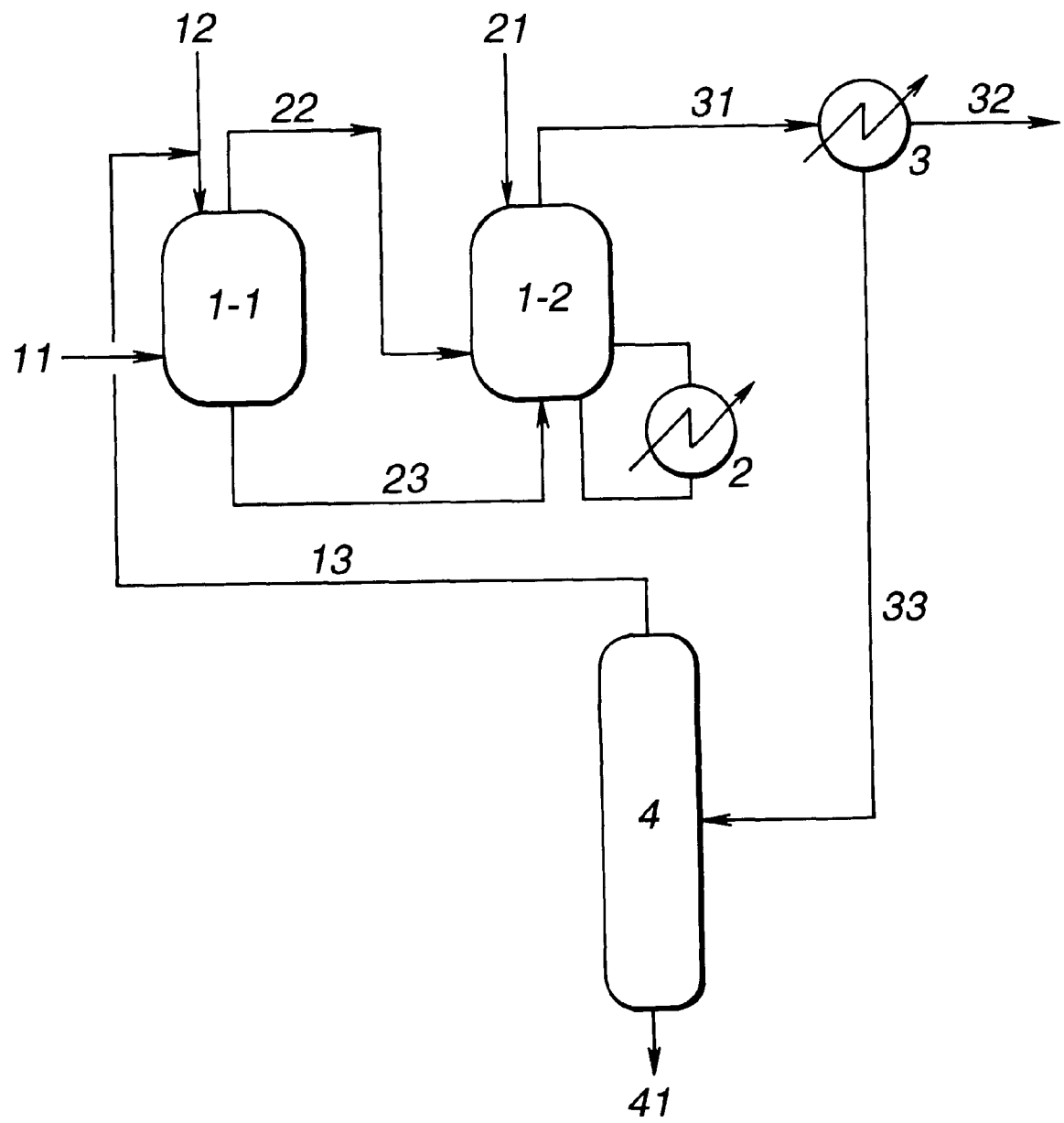
FIG. 1 schematically illustrates one exemplary system for preparing methyl chloride according to the invention.

According to the invention, methyl chloride is prepared by effecting liquid-phase reaction between hydrogen chloride and methanol in the absence of a catalyst. The liquid-phase reaction is effected in at least two divided stages, that is, at least an early stage and a last stage. The number of reaction stages or reactors is not particularly limited as long as more than one stage is included. Usually, two to four stages, especially two or three stages are used. In most cases, satisfactory results are obtained with two stages.

The early stage of liquid-phase reaction, especially reaction prior to the last stage, is effected in a stoichiometrically excessive hydrogen chloride atmosphere, that is, using a stoichiometrically smaller amount of methanol relative to hydrogen chloride. The last stage of liquid-phase reaction is effected in a stoichiometrically excessive methanol atmosphere, that is, using a stoichiometric excess of methanol relative to hydrogen chloride as a result of additional feed of methanol, thereby reducing the concentration of hydrogen chloride in the reactor below the azeotropic concentration. In general, the total molar ratio of methanol to hydrogen chloride is from about 1.0 to about 2.0. According to the invention, it is preferred that the molar ratio is from 0.7 to 0.95, especially from 0.8 to 0.95 prior to the last stage, and the total molar ratio during the overall process including the last stage is from 1.05 to 1.4, especially from 1.05 to 1.3. Outside these ranges, there is a tendency that below the ranges, the conversion of hydrogen chloride becomes low, and beyond the ranges, the amount of dimethyl ether by-product becomes larger. With these molar ratios met, it is further preferred that the liquid phase in the early stage, especially the liquid phase prior to the last stage have a hydrogen chloride concentration of 22 to 30% by weight and a methanol concentration of 3 to 8% by weight, and the liquid phase during the last stage have a hydrogen chloride concentration of 8 to 17% by weight and a methanol concentration of 1 to 5% by weight. This concentration setting enables an improvement both the reaction rate and the conversion of hydrogen chloride while suppressing the formation of dimethyl ether by-product.

The reaction temperature is preferably 90 to 130° C., especially 100 to 110° C. in the early stage, especially prior to the last stage, and preferably 100 to 150° C., especially 110 to 130° C. in the last stage because a sufficient reaction rate is ensured and the formation of by-products is suppressed. The reaction time is not critical although the total reaction time is generally about 2 to 8 hours, especially about 3 to 4 hours. The reaction time in the last stage is about 2 to 8 hours, especially about 3 to 4 hours. Other reaction conditions are as in conventional processes.

Since the methyl chloride preparing process of the invention is carried out in the absence of a catalyst, the reactants used therein need not be of high purity. Even a reactant containing an impurity capable of exhausting or poisoning the catalyst can be used. For example, a hydrogen chloride by-product resulting from a silicone manufacturing plant and containing silanes and silicones may be used as the reactant. Unreacted methanol may be recycled for reuse. For example, where the last stage reactor contains methyl chloride and by-product water as the outcome of reaction and unreacted methanol fed in excess, these components are gasified and distilled off the last stage reactor, the resulting crude gas is separated into methyl chloride gas and an aqueous methanol solution, the aqueous methanol solution is separated into methanol and water, and the methanol is recycled for reuse as a reactant.

FIG. 1 shows one exemplary preferred system for use in carrying out the process of the invention although the invention is not limited thereto. Using this system, methyl chloride can be advantageously prepared as follows.

The system includes a first stage reactor 1—1, a last stage reactor 1-2, a hydrogen chloride source (11), methanol sources (12, 21), a reboiler 2, a condenser 3, and a distillation column 4, which are connected through conduits as illustrated in FIG. 1.

Two reactants, hydrogen chloride and methanol are fed into the first stage reactor 1—1 through conduits 11 and 12. The amounts of the reactants are adjusted such that methanol is stoichiometrically less than hydrogen chloride, establishing a hydrogen chloride excess atmosphere.

In the first stage reactor 1—1, hydrogen chloride reacts with methanol to form methyl chloride. This reaction is not complete. A gaseous mixture composed mainly of methyl chloride and a liquid mixture composed mainly of water by-product and unreacted reactants are transferred to the last stage reactor 1-2 through conduits 22 and 23, respectively.

Methanol is additionally fed to the last stage reactor 1-2 through a conduit 21 such that methanol is stoichiometrically excess to hydrogen chloride, establishing a methanol excess atmosphere. The solution in the reactor 1-2 is heated by the reboiler 2 for promoting reaction and selectively distilling off water.

The crude gas produced in the last stage reactor 1-2 is delivered through a conduit 31 to the condenser 3 where it is cooled for condensation and separated into methyl chloride gas and an aqueous methanol solution containing a minor amount of unreacted hydrogen chloride. The methyl chloride gas is taken out through a conduit 32.

The aqueous methanol solution separated by condensation is delivered through a conduit 33 to the distillation column 4 where it is separated into methanol and water containing a minor amount of unreacted hydrogen chloride. Substantially pure methanol emerging from the top of the column 4 is fed back to the first stage reactor 1—1 through a conduit 13 for reuse as the reactant. The by-product water containing a minor amount of unreacted hydrogen chloride is discharged from the column bottom through a conduit 41.

In this system, the amount of methanol fed is manually or automatically adjusted relative to the amount of hydrogen chloride fed by monitoring the flow rates of hydrogen chloride and methanol by means of flow meters (not shown)

attached to the conduits 11, 12 and 21. Alternatively, the amount of hydrogen chloride fed is adjusted relative to the amount of methanol fed. It is also effective to adjust the feed ratio of hydrogen chloride and methanol by sampling out the liquids in the reactors, analyzing the samples for the concentrations of hydrogen chloride and methanol, and effecting flow rate control in accordance with the analytic results.

According to the invention, methyl chloride can be prepared through reaction of hydrogen chloride with methanol in an industrially advantageous manner, that is, at a high conversion of hydrogen chloride while suppressing the formation of dimethyl ether by-product.

EXAMPLE

Examples of the invention are given below by way of illustration and not by way of limitation. All parts are by weight.

Example 1

The inventive process was carried out in an experimental system as shown in FIG. 1.

Anhydrous hydrogen chloride was fed to the first stage reactor 1—1 through the conduit 11 at a flow rate of 3,500 g/hr., and methanol was fed to the first stage reactor 1—1 through the conduit 12 at a flow rate of 2,460 g/hr. (including methanol recycled through the conduit 13). Additional methanol was fed to the last stage reactor 1-2 through the conduit 21 at a flow rate of 770 g/hr. The first and last stage reactors 1—1 and 1-2 were maintained at internal temperatures of 105° C. and 120° C., respectively. After a steady state was reached, methyl chloride was delivered through the conduit 32 at a flow rate of 4,760 g/hr., which corresponded to a conversion of hydrogen chloride of 98.2%. The total molar ratio of methanol to hydrogen chloride was 1.05. The methyl chloride product contained 0.3% by weight of dimethyl ether.

Example 2

Example 1 was repeated except that the amounts of methanol fed to the first and last stage reactors were changed.

Anhydrous hydrogen chloride was fed to the first stage reactor 1—1 through the conduit 11 at a flow rate of 3,500 g/hr., and methanol was fed to the first stage reactor 1—1 through the conduit 12 at a flow rate of 2,770 g/hr. (including methanol recycled through the conduit 13). Additional methanol was fed to the last stage reactor 1-2 through the conduit 21 at a flow rate of 620 g/hr. The first and last stage reactors 1—1 and 1-2 were maintained at internal temperatures of 105° C. and 120° C., respectively. After a steady state was reached, methyl chloride was delivered through the conduit 32 at a flow rate of 4,810 g/hr., which corresponded to a conversion of hydrogen chloride of 99.2%. The total molar ratio of methanol to hydrogen chloride was 1.1. The methyl chloride product contained 0.3% by weight of dimethyl ether.

Comparative Example 1

Using the same system as in Example 1, reaction was carried out using a stoichiometrically smaller amount of methanol relative to the hydrogen chloride feed.

Anhydrous hydrogen chloride was fed to the first stage reactor 1—1 through the conduit 11 at a flow rate of 3,500 g/hr., and methanol was fed to the first stage reactor 1—1 through the conduit 12 at a flow rate of 2,460 g/hr. (including methanol recycled through the conduit 13). Additional methanol was fed to the last stage reactor 1-2 through the conduit 21 at a flow rate of 310 g/hr. The first and last stage reactors 1—1 and 1-2 were maintained at internal temperatures of 105° C. and 120° C., respectively. After a steady state was reached, methyl chloride was delivered through the conduit 32 at a flow rate of 4,040 g/hr., which corresponded to a conversion of methanol of 92.6%. The total molar ratio of methanol to hydrogen chloride was 0.9. The methyl chloride product contained 0.3% by weight of dimethyl ether.

Comparative Example 2

Figure 2:
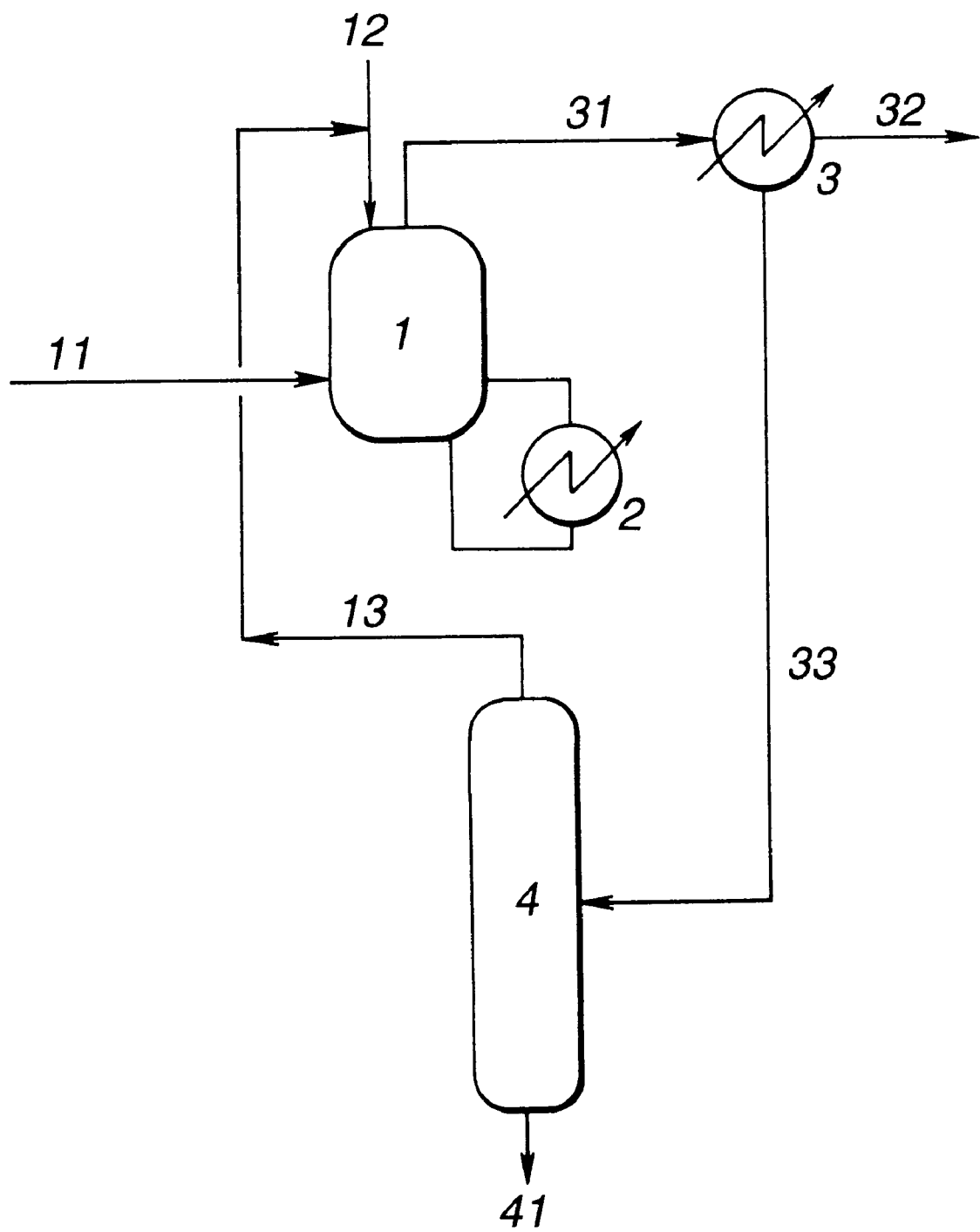
FIG. 2 is a schematic view of a comparative system.

This Example used a single stage reactor as shown in FIG. 2. The system of FIG. 2 is different from FIG. 1 in that only a single reactor 1 is included while a condenser 3 and a distillation column 4 are similarly connected to the reactor.

Reactants, hydrogen chloride and methanol were fed to a reactor 1 through the conduits 11 and 12, respectively. The liquid in the reactor was heated by a reboiler 2 for promoting reaction and gasifying the entire contents, which were distilled out of the reactor 1.

Thereafter, as in Example 1, the crude gas product was fed to the condenser 3 where it was cooled and separated into methyl chloride gas and an aqueous methanol solution. The aqueous methanol solution was distilled in the column 4 whereby substantially pure methanol was recovered and fed back to the reactor 1 for reuse. The reactor volume was equal to the sum of the volumes of the first and last stage reactors in Example 1.

In this single reactor system, anhydrous hydrogen chloride was fed to the reactor 1 through the conduit 11 at a flow rate of 3,500 g/hr., and methanol was fed to the reactor 1 through the conduit 12 at a flow rate of 3,390 g/hr. (including methanol recycled through the conduit 13). The reactor I was maintained at an internal temperature of 120° C. Methyl chloride was delivered through the conduit 32 at a flow rate of 4,250 g/hr., which corresponded to a conversion of hydrogen chloride of 87.7%. The total molar ratio of methanol to hydrogen chloride was 1.1. The methyl chloride product contained 1.0% by weight of dimethyl ether.

The results are summarized in Table 1.

TABLE 1

|  |  | E1 | E2 | CE1 | CE2 |
|---|---|---|---|---|---|
| HCl feed (g/h) |  | 3500 | 3500 | 3500 | 3500 |
| Early stage | Methanol feed (g/h) | 2460 | 2770 | 2460 | 3390 |
|  | HCl concentration (%) | 26.2 | 24.5 | 26.2 | 15.3 |
|  | Methanol concentration (%) | 4.8 | 6.5 | 4.8 | 6.4 |
| Last stage | Methanol feed (g/h) | 770 | 620 | 310 | — |
|  | HCl concentration (%) | 12.2 | 11.7 | 13.9 | — |
|  | Methanol concentration (%) | 2.1 | 2.3 | 1.9 | — |
| Methanol/HCl molar ratio | Early stage | 0.8 | 0.9 | 0.8 | — |
|  | Total | 1.05 | 1.1 | 0.9 | 1.1 |
| Methyl chloride produced (g/h) |  | 4760 | 4810 | 4040 | 4250 |
| Conversion (%) |  | 98.2 | 99.2 | 92.6 (methanol basis) | 87.7 |

Japanese Patent Application No. 139395/1997 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A process for preparing methyl chloride by effecting liquid-phase reaction between hydrogen chloride and methanol in the absence of a catalyst, wherein the liquid-phase reaction is effected in divided stages including at least an early stage and a last stage, the early stage of liquid-phase reaction is effected in a stoichiometrically excessive hydrogen chloride atmosphere, and the last stage of liquid-phase reaction is effected in a stoichiometrically excessive methanol atmosphere.

2. The process of claim 1 wherein the molar ratio of methanol to hydrogen chloride is from 0.7 to 0.95 prior to the last stage, and the molar ratio of methanol to hydrogen chloride is from 1.05 to 1.4 throughout the process including the last stage.

3. The process of claim 2 wherein the liquid phase prior to the last stage has a hydrogen chloride concentration of 22 to 30% by weight and a methanol concentration of 3 to 8% by weight, and the liquid phase during the last stage has a hydrogen chloride concentration of 8 to 17% by weight and a methanol concentration of 1 to 5% by weight.

4. The process of claim 1 wherein the reactor of the last stage contains methyl chloride and by-product water as the outcome of reaction and unreacted methanol fed in excess, said process further comprising the steps of gasifying and distilling these components off from the last stage reactor, separating the resulting crude gas into methyl chloride gas and an aqueous methanol solution, separating the aqueous methanol solution into methanol and water, and recycling the methanol for reuse as a reactant.

5. The process of claim 1 wherein hydrogen chloride which is obtained as a by-product in a silicone manufacturing plant is used as a reactant.

6. The process of claim 5 wherein the hydrogen chloride used as a reactant contains silanes and silicones.

7. The process of claim 1, wherein the reaction is conducted in two to four stages.

8. The process of claim 1, wherein the reaction temperature is 90 to 130° C. in the early stage and 100 to 150 ° C. in the last stage.

9. The process of claim 1, wherein the total reaction time is from 2 to 8 hours.

* * * * *